United States Patent [19]
Fujii

[11] 3,943,135
[45] Mar. 9, 1976

[54] OLIGOETHYLENEPIPERAZINES
[75] Inventor: Kouki Fujii, Yokohama, Japan
[73] Assignee: Sanraku-Ocean Co., Ltd., Tokyo, Japan
[22] Filed: Sept. 12, 1973
[21] Appl. No.: 396,396

[30] Foreign Application Priority Data
Sept. 13, 1972 Japan.................... 47-91179

[52] U.S. Cl. ........ 260/268 PL; 260/268 S; 424/250
[51] Int. Cl.²...................................... C07D 295/12
[58] Field of Search....... 260/268 PL, 268 S, 268 R, 260/268 BI

[56] References Cited
UNITED STATES PATENTS

| | | | |
|---|---|---|---|
| 2,513,026 | 6/1950 | Jacob et al. ..................... | 260/268 S |
| 2,756,231 | 7/1956 | Bach et al. ..................... | 260/268 R |
| 3,203,952 | 8/1965 | Paquette........................ | 260/268 S |
| 3,269,999 | 8/1966 | Moore et al. .................. | 260/268 BI |
| 3,532,646 | 10/1970 | Antikow et al. ............... | 260/268 BI |
| 3,565,837 | 2/1971 | Drawert et al................ | 260/268 BI |

Primary Examiner—Richard J. Gallagher
Assistant Examiner—Jose Tovar
Attorney, Agent, or Firm—James C. Haight

[57] ABSTRACT

Oligoethylenepiperazines and their derivatives of the formula

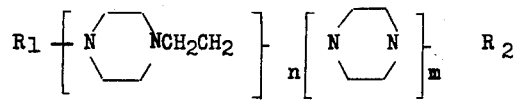

wherein
$n$ is a positive integer of 1 to 7 inclusive;
$m$ is zero or one when $n=1$, or $m$ is one when $n=2\sim7$
$R_1$ is hydrogen, benzenesulfonyl or benzenesulfonyl ring substituted by at least one member selected from the group consisting of lower alkyl of 1–4 carbon atoms, nitro and amino;
$R_2$ is halogen when $m$=zero and hydrogen, benzenesulfonyl or benzenesulfonyl ring substituted by at least one member selected from the group consisting of lower alkyl of 1–4 carbon atoms, nitro and amino when $m$=one; and the cationic salts thereof are useful as anion exchange oligomers, antihelmintic compounds, and intermediates for the preparation of polymers and fine industrial chemicals.

9 Claims, 16 Drawing Figures

OLIGOETHYLENEPIPERAZINES

BACKGROUND

This invention relates to oligoethylenepiperazines and their derivatives as well as to methods for the preparation and use thereof.

Several polyalkylene piperazines are known as intermediates for the preparation of polymers and fine industrial chemicals, e.g., surfactants, corrosion inhibitors, wetting agents, detergents, flocculating and/or dispensing agents, veterinary antihelminthic agents, and monomers which polymerize by condensation with various comonomers reactive with the secondary amine function, e.g., alkyl and aryl diisocyanetes and alkyl and aryl diacid chlorides.

Polymeric cations are widely used as anion exchange resins, electron conductors, wetting agents, etc. The "Dowex" synthetic ion exchange resins are prepared from styrene-divinylbenzene copolymers having a large number of ionizable or functional groups attached to this hydrocarbon material by ring substitution. The "Amberlite" ion exchange resins are a series of various crosslinked polymers in bead form which are widely used industrially. Both of these types of anion exchange resins are generally characterized as styrene and polysulfonic acid types bearing aines in the side chains. Anion exchange polymers or oligomers having cationic amines in the main skeletal chain are more stable than the above two types of resins to heat and alkalis. They are also advantageous ion exchangers since they have no unsaturated radicals which exert undesirable adsorption.

4,4'-disubstituted-1,1'-ethylene dipiperazines and their salts have been described in U.S. Pat. No. 2,756,231 as useful antispasmodics and gastric inhibitors which are prepared by reacting a 1-substituted piperazine with a vicinal dihaloalkane in the presence of a suitable base. The ethylene linkage bridging the two piperazine rings in these compounds is mono - or disubstituted, and the compounds themselves are viscous oils.

Piperazine-containing polymers containing $C_3$ to $C_{12}$ polymethylene radicals bridging the piperazine rings have been described in U.S. Pat. No. 3,532,646. These oligomers are prepared by the polycondensation of an N,N'-bis-β-hydroxyethyl diamine with ring-formation dehydration; this process is inapplicable to ethylene groups, as only hydroxyethylpiperazine is formed. The compounds prepared according to the aforementioned U.S. Pat. No. 3,532,646, represent a mixture of compounds of varying molecular weight. Because of difficulties in separation into each component compound, they are poorly suited as an intermediate for further practical chemical preparations.

Certain polamines containing repeating ethylene-piperazine units in the molecule can by synthesized by the ring-opening polymerization of triethylenediamine (1,4-diazabicyclo-2,2,2-octane) with the aid of an aryl-sulfonylchloride initiator, as has been described in H. K. Hall, Jr., J. Org. Chem. 28:223 (1963).

As with most polymerization reactions, this ring-opening process continues progressively to form predominantly polymers having relatively high molecular weights, and the resultant product invariably comprises a mixture of many different oligomers. Because of these drawbacks and the difficulties of separating the polymer product into a particular molecular weight component, these products are of only limited value as starting materials for the synthesis of further compounds therefrom.

Since compounds of this class have a wide variety of potential applications, it would be highly desirable to have available a method whereby low molecular weight ethylenepiperazine oligomers could be prepared in such a way as to tailor the molecular weight of the final product to desirable lower values than are obtained by this condensation polymerization method. The present invention fills such a need.

OBJECTS OF THE INVENTION

Accordingly, it is a general object of this invention to provide new oligoethylene piperazines and processes for the preparation and use thereof.

Another object of this invention is to provide a process for accurately controlling the degree of polymerization and final product molecular weight in the preparation of oligoethylenepiperazines.

A further object of this invention is to provide antihelmintic compositions based on antihelmintically effective oligoethylene piperazines.

An additional object of this invention is to provide anion exchange oligomers characterized by containing cationic amines in the main oligomer skeletal chain.

Still another object of this invention is to provide novel quaternary ammonium salts.

A supplemental object of this invention is to provide protected oligoethylene piperazines wherein the terminal secondary cyclic amino groups are masked or blocked in an easily reversible manner.

Other objects and advantages of this invention will become apparent to those skilled in the art upon further study of the specification and appended claims.

SUMMARY OF THE INVENTION

Briefly, the above and other objects are attained in one aspect of the present invention by providing compounds of general Formula I wherein
n is a positive integer of 1 to 7 inclusive;
m is zero or one when n=1, or m is one when n=2~7
$R_1$ is hydrogen, benzenesulfonyl or benzenesulfonyl ring substituted by at least one member selected from the group consisting of lower alkyl of 1–4 carbon atoms, nitro and amino;
$R_2$ is halogen when m=zero and is $R_1$ when m=one; and the cationic salts thereof.

BRIEF DESCRIPTION OF THE DRAWINGS

The above and other objects of the invention will become more fully apparent to those skilled in the art from the following Detailed Discussion, taken in conjunction with the annexed Drawings which illustrate infrared (IR) and nuclear magnetic resonance (NMR) spectra of compounds prepared according to this invention, wherein.

DETAILED DISCUSSION

Preferred compounds of the present invention are those compounds of Formula I meeting one or more of the following criteria:

a. Compounds in which $m$=zero and $R_2$ =Cl, Br or I;
b. Compounds in which $R_1 = R_2$;
c. Compounds in which $R_1$ and $R_2$ are both hydrogen;
d. Compounds in which $R_1$ and $R_2$ are each benzenesulfonyl or benzenesulfonyl ring substituted by at least one member selected from the group consisting of lower alkyl of 1–4 carbon atoms, nitro and amino;
e. Compounds in which $R_1$ and $R_2$ are each benzenesulfonyl ring substituted by at least one member selected from the group consisting of methyl, nitro and amino;
f. Compounds in which $n = 1$; and
g. Compounds wherein $R_1$ and $R_2$ are both hydrogen and in which at least one tertiary amino group thereof is in the form of a quaternary salt.

While the physical properties of the compounds according to Formula I vary somewhat depending on their exact structure and the particular value of $n$, the compounds in general are characterized by being solids at room temperature melting at above 100°C which can be recrystallized from dilute aqueous ammonia (pH 9 –11). They exhibit defined melting points but generally discolor and decompose when $n = 6$ or 7. Their IR absorption spectra show absorption bands characteristic of an N,N' disubstituted piperazine ring at 7.5$\mu$, 7.6$\mu$ and 7.8$\mu$, 7.9$\mu$ (FIGS. 1–3, 5, 7, 9, 11, 13, and 15).

The compounds of Formula I are soluble to a decreasing extent with increasing values for $n$ in solvents such as chloroform, DMF (N,N dimethylformamide) and ethanol. They are generally insoluble in solvents such as n-hexane, peteroleum-ether and cyclohexane.

Those compounds wherein $R_1$ and $R_2$ are H contain a terminal secondary amine group at each end of the oligoethylenepiperazine molecule, and can in that sense be considered telomers. These secondary amine groups, like piperazine, are very reactive and readily susceptible to secondary amine addition reactions such as acylations, alkylations, and the formation of amides, sulfonamides and N-nitrosamines. For example, acetylation can be readily effected by adding excess acetic anhydride, heating to 100°C, and removing excess acetic acid followed by treating with a strong base to form the diacetylated oligoethylenepiperazines.

The Shotten-Baumann type reaction is also available to yield acylated derivatives of the present compounds. For example, oligoethylenepiperazine dissolved in a suitable organic solvent is reacted at room temperature with a suitable acid halide, e.g., a fatty acid chloride whereby the ester is introduced, e.g., to form an oligoethylenepiperazine N-fatty acid derivative. The use of diacid halide in place of acid halide renders new polyamine polyamide compounds having various usages in the field of organic chemicals, especially polymer synthesis. Alkylation and aralkylation at the terminal amines also gives a series of compounds of chemical interest.

A particularly unique feature of oligoethylenepiperazine as compared to piperazine monomer is that it has tertiary amines in the inside of both ends. These tertiary amines can be easily converted to the quaternary form, e.g., by the Menschutkin Reaction with halogenated organic compounds such as alkylhalides and aralkylhalides. Since the oligoethylenepiperazines of the present description have a different number of tertiary amines depending on the particular n-values, an entire series of compounds having different cation values can thus be produced.

Suitable quaternizing agents are those which contain an active halogen atom attached to a carbon atom in a compound which is not an acid. Such halogen-containing quaternizing agents include but are not limited to the various alkyl halides such as methyl iodide, methyl bromide, ethyl iodide, propyl iodide, hexyl iodide, nonyl bromide, cetyl bromide; the various alkylene halides such as ethylene iodide, ethylene bromide, propylene chloride, butene bromide, octene bromide; the various substituted alkanes and cycloalkanes necessarily including the above alkyl and alkylene halides, which contain at least one hydrogen atom attached to a carbon atom, such as bromoform, chloroform, 1,2-dichloropropane, 1,2-dibromobutane, ethylene chlorohydrin, acetyl chloride, iodoform, chloroacetyl chloride; the various substituted aromatic compounds such as picryl chloride, benzoyl chloride, phenyl chloride, benzene sulfonyl chloride, benzyl chloride, benzal chloride, and benzotrichloride.

The amount of quaternizing agent employed will generally be in the range of 2 – 4 mol ratio based on the basic nitrogen units in the polymer. The amount of quaternizing agent employed in any particular case will depend largely upon the type of product desired.

For the preparation of oligoethylenepiperazines of this invention, an N-protected piperazine is essential as a starting material. The protection is conventionally effected by arylsulfonylation. Reaction of a benzene sulfonylhalide having the general Formula II

II

(wherein R' is H, CH$_3$, NO$_2$, NH$_2$ and X is a halogen atom) with piperazine in the presence of a base and in a polar solvent gives both the N-mono-arylsulfonyl and the N,N'-diarylsulfonyl derivatives. For instance, p-toluenesulfonylchloride (tosylchloride) reacts with piperazine in the presence of triethylamine (CH$_3$CH$_2$)$_3$N in a polar solvent such as DMF (N,N-dimethylformamide) and THF (tetrahydro-furan) to give a mixture of N-p-toluenesulfonylpiperazine and N,N'-di-p-toluenesulfonylpiperazine.

The present inventor has found that monosubstitution of piperazine with arylsulfonylchloride is advantageously effected only by conducting the reaction in a nonpolar solvent such as benzene. For example, N-tosylpiperazine is obtained in a high yield (99.5%) by reacting tosylchloride with piperazine in the presence of a tertiary amine such as triethylamine in benzene.

The equation is as follows:

By a nonpolar solvent is meant an aprotic, normally liquid inert organic diluent which is neither water miscible nor appreciably water soluble, i.e., less than about 0.7 grams of the solvent dissolves in 100 ml of water at room temperature. Suitable such nonpolar solvents are well known in the art and include but are not limited to alkanes, e.g., hexane, heptane, octane, etc.; cycloalkanes, e.g., cyclopentane, cyclohexane, cycloheptane, etc.; aromatic hydrocarbons, e.g., benzene, decahydronaphthatene etc.; alkylated aromatic hydrocarbons, e.g., toluene, the xylenes, ethylbenzene, etc.; ethers, e.g., diethylether; and nonpolar halogenated hydrocarbons, e.g., carbon tetrachloride.

Since hydrogen halide is liberated as a byproduct in the above reaction, provision must be made for its neutralization. This can be accomplished by using an excess of piperazine in the reaction mixture or more economically by the addition a stoichiometric excess of a suitable Lewis base, preferably a tertiary amine such as a trialkylamine, e.g., triethylamine, tri-n-propylamine and tri-n-butylamine or an N-alkyl-hetero-cyclic amine, e.g., N-ethylpiperidine and N-ethylmorpholine, either alone or in admixture. As with the nonpolar solvent, it is preferable that the tertiary amine be anhydrous.

In accordance with the present invention, oligoethylenepiperazine can be produced by the following three steps:

1. Production of N-arylsulfonyl-N'-β-haloethylenepiperazine: N-arylsulfonyl-N'-β-haloethylenepiperazine can be produced by conducting either reaction (a) or (b).

a. an arylsulfonylhalide having the general Formula II is reacted with piperazine in the presence of an acid acceptor in a nonpolar solvent to produce an N-arylsulfonylpiperazine of Formula III, and the N-arylsulfonylpiperazine thus produced is then reacted with an ethylene dihalide having the formula XCH₂CH₂X' (wherein X and X' are the same or preferably different halogen atoms selected from the group consisting of Cl, Br and I, e.g., 1-bromo-2-chloroethane, 1-iodo-2-chloroethane, 1-iodo-2-bromoethane, 1,2-dibromoethane, etc.,) in the presence of an acid acceptor in a nonpolar solvent to produce N-aryl-sulfonyl-N'-β-haloethylenepiperazine having the general Formula IV:

wherein R' is H, CH₃, NO₂ and NH₂ and X is Cl, Br or I. As described hereunder, the compounds of Formulae III and IV are used in the second step.

b. An Arylsulfonylhalide of Formula II is reacted with triethylenediamine in a nonpolar solvent such as benzene to produce N-arylfulfonyl-N'-β-haloethylenepiperazine.

As clearly shown above, N-arylsulfonyl-N'-β-haloethylenepiperazine having a desirable halogen atom can be obtained by employing an ethylenedihalide having the corresponding X. When X and X' are different, X in the above formulae will signify the lower molecular weight halide.

2. Production of α, ω-diprotected oligoethylenepiperazines: In contrast to the first step, this second step is carried out in a polar organic solvent which need not be anhydrous. As a polar solvent, protic solvents such as methanol, ethanol, propanols, and butanols can be used as well as aprotic solvents such as dioxane, dimethylformamid, dimethylsulfoxide, etc., and aqueous azeotropes, e.g., 95% ethanol.

The compounds can be obtained by conducting reactions selected from the following steps:

a. The N-arylsulfonylpiperazine (III) produced by (a) in the first step is reacted with the N-arylsulfonyl-N'-haloethylenepiperazine (IV) produced by (a) in the first step in the presence of an acid acceptor in a polar solvent under reflux to produce a 1,1'-ethylene-bis(4-arylsulfonylpiperazine) of Formula V:

b. 2 mol of N-arylsulfonylpiperazine (III) is reacted with 1 mol of ethylene-dihalide in the presence of an acid acceptor in a polar solvent under reflux to produce 1,1'-ethylene-bis (4-arylsulfonylpiperazine) (V);

c. 2 mol of N-arylsulfonyl-N'-β-haloethylenepiperazine (IV) is reacted with 1 mol of piperazine in the presence of an acid acceptor in a polar solvent under reflux to produce an α,ω-diprotected oligomer of Formula VI:

d. 2 mol of N-arylsulfonyl-N'-β-haloethylenepiperazine is reacted with 1 mol of an α,ω-unprotected oligoethylenepiperazine in the presence of an acid acceptor in a polar solvent under reflux to produce an α,ω-diprotected oligomer (VII):

As clearly shown in the above reactions, various kinds of desirable oligomer can be obtained as $\alpha,\omega$-diprotected oligomers. In accordance with these reactions, triethylamine is preferably used as the acid acceptor, although the various kinds of tertiary amines which are suitable in the production of N-arylsulfonyl-N'-$\beta$-haloethylenepiperazine described in the first step can be also used as the acid acceptor.

3. Production of final product; fission of the protective arylsulfonyl group.

The $\alpha,\omega$-diprotected tertiary sulfonamide oligomers (V, VI, VII) obtained in the second step are subjected to the reductive reaction to remove arylsulfonyl radicals attached to the secondary amine radicals at both ends of the molecule of the oligomer in order to obtain the final products. For instance, in the reaction from the $\alpha,\omega$di-protected oligomer V or VII where $n=1$ to the product I where $n=1$, acid hydrolysis, alkali hydrolysis and hydrogen addition can be employed to remove the protecting arylsulfonyl radicals. Furthermore, the inventor has found that sodium in alcohol (such as n-butanol, isoamylalcohol and n-amylacohol) and sodium in liquid ammonia can be advantageously employed as the reducing agent which gives high yields, as reported by W. R. Vaughan, et al. J. Org. Chem. 26:138, (1961) the contents of which are incorporated by reference herein. While the tosyl radical is employed as the masking arylsulfonyl radical in the above case, various aromatic sulfonyl radicals such as benzene-sulfonyl, o-nitro-benzenesulfonyl, o-methyl benzenesulfonyl, etc. can be also employed as the protecting agent.

Some impurities brought about by undesirable side reactions during the said three steps are sometimes contained in the final liquid. However, by carrying out the process according to this invention, one can mainly obtain the target oligomer with very little oligomer having different molecular weights from the target. Since most of the undesirable product in the final step is protected oligomer, purification is easily carried out employing conventional methods, because their chemical and physical properties such as solubility are considerably different from the target oligomer. In other words, pure products of any desired molecular weight can be synthesized according to this invention.

So, in scheduling to produce the target product, for instance to produce the product (I) ($n=7$)

the steps can be employed as follows.

The following flow sheet illustrates the stepwise preparation of oligoethylenepiperazines of $n=1$ through 7 inclusive; the same basic techniques can be employed to obtain any finally desired value for $n$ e.g. up to 20, 100 or even higher.

Thus, according to this invention, the new compounds, oligoethylenepiperazines, having desired numbers of tertiary amine radicals in the molecule can be produced by selecting the starting materials in combination with the reactions explained above.

Due to their antihelmintic activity, the compounds of this invention are useful as antihelmintics in veterinary medicine. In addition to their use in vitro, they can be employed, for example, in the enteral therapy of helminthiasis in substantially the same manner as other antihelmintic piperazine derivatives.

The compounds of this invention can be employed in mixture with conventional excipients, i.e., pharmaceutically acceptable organic or inorganic substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, neutral or alkaline buffers, coloring, flavoring and/or aromatic substances and the like which do not deleteriously react with the active compounds.

For enteral application, particularly suitable are tablets, dragees, or capsules having talc and/or a carbohydrate carrier or binder or the like, the carrier preferably being lactose and/or corn starch and/or potato starch. A syrup, elixir or the like can be wherein a sweetened vehicle is employed. Sustained release compositions can be formulated including those wherein the active compound is protected with differentially degradable coatings, e.g., by microencapsulation, multiple coatings, etc.

In this regard, they can be employed in substantially the same manner as the known anthihelmintic piperazines.

Use of the oligoethylene-piperazines for the treatment of helminthiasis in animals according to the present invention involves intestinal contact of the infecting helminth with the drug. Dosage is preferably by the oral route since the major site of infection in ordinarily the intestinal tract. It is of course possible to administer these drugs rectally, but of course, this method is not as convenient as oral medication. One of the attributes of these new drugs is that they are highly effective orally. The daily dose required varies with the particular oligoethylene-piperazine employed and the animal which is being treated.

Administration to animals can best be effected by mixing the drug with the feed. Thus, the required dose for the animal is calculated on the basis of the known formula and the drug is then blended with all or a portion of the animal's daily ration. The oligomers are generally supplied as the substantially pure substance for this purpose. However, they can be diluted with inert carriers such as starch, lactose, etc. This is preferred with small animals where the total dosage is low since blending of only a few milligrams of drug with a relatively large amount of feed is inconvenient. For this purpose a dry solid composition containing the calculated dosage of oligomers is blended with a convenient amount of carrier generally from about 1 to 10 parts by weight based on the weight of the active compound.

It will be appreciated that the actual preferred amounts of active compounds used will vary according to the specific compound being utilized, the particular compositions formulated, the mode of application, and the particular situs and organism being treated. Optimal application rates for a given set of conditions can be ascertained by those skilled in the art using conventional dosage determination tests in view of the above guidelines.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight. The values obtained in elemental analyses are within commonly accepted limits of error.

EXAMPLE 1

Production of p-toluenesulfonylpiperazine (Compound III):

Piperazine 43 g (0.5 mol) and triethylamine 69 ml (0.55 mol) were dissolved with agitation in 600 ml of anhydrous benzene maintained at a temperature of 35°–40°C in a 3-liter flask. A solution of 19.06 g (0.1 mol) of p-toluenesulfonylchloride (Formula II) dissolved in 600 ml of anhydrous benzene was added dropwise into the amine solution over a period of about 2 hours with stirring. Stirring was continued until the precipitation of triethylamine-HCl ceased. The reaction mixture was filtered to remove the precipitate and then the filtrate was dried under reduced pressure, yielding a white powder.

Figure 1:
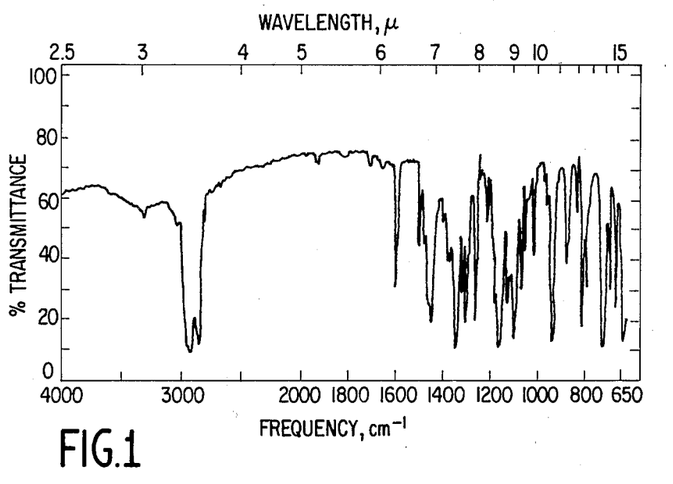
FIG. 1 shows the IR spectrum (Nujol) of p-toluenesulfonylpiperazine from Example 1.

Stripping off unreacted piperazine by sublimation under reduced pressure (20 mm Hg) from the white powder gave a pale yellow powder which was recrystallized from benzene-petroleum ether (6 : 4). 23.9 g of white plate crystals of p-toluenesulfonylpiperazine (Formula III) were obtained. The yield was 99.5% of p-toluenesulfonylchloride. Melting point: 108.5°~109.5°C. The IR spectrum in Nujol is shown in FIG. 1.

EXAMPLE 2

Production of N-β-chloroethyl-N′-p-toluenesulfonylpiperazine (Compound IV):

(II)

(IV)

Figure 2:
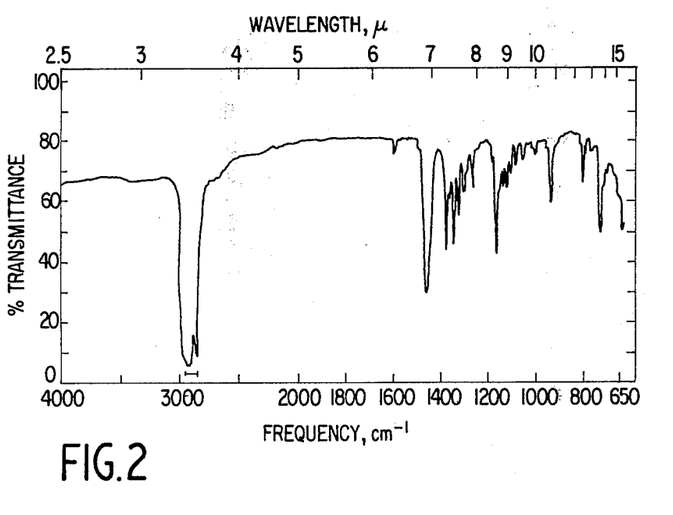
FIG. 2 shows the IR spectrum (Nujol) of N-β-chloroethyl-N'-p-toluenesulfonylpiperazine from Example 2.
Figure 3:
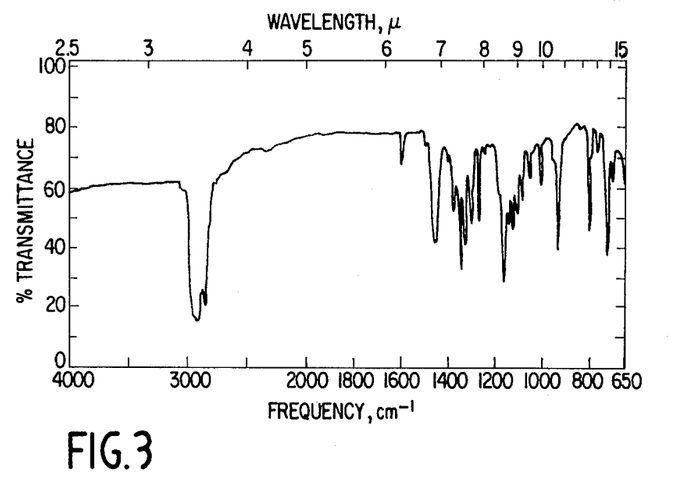
FIGS. 3 and 4 show the IR (Nujol) and NMR spectrum ($d_6$- DMSO) respectively, of 1,1'-ethylene-bis (4-p-toluenesulfonylpiperazine) from Example 4($n$=1)

Triethylenediamine 22.4g (0.2 mol) was dissolved in 300 ml of anhydrous benzene in a 1 liter three-necked flask and heated to reflux. A solution of 38.1 g (0.2 mol) of p-toluenesulfonylchloride in 300 ml of anhydrous benzene was added dropwise into the flask over a period of about one hour. Heating to reflux was continued for a further 4 hours. After completion of the reaction, the solution was filtered. The filtrate was kept standing at room temperature, and white needle crystals precipitated out. By filtering and drying the crystals, N-β-chloroethyl-N'-p-toluenesulfonylpiperazine 39.6 g (yield: 65.4%) was obtained. Melting point: 137.5°~138.5°C. Elemental analysis: Calculated: C 51.57%; H b 6.28%; N 9.25%; Cl 11.73%. Found: 51.66%; N 9.2%; Cl 11.84%. The IR spectrum in Nujol is shown in FIG. 2.

EXAMPLE 3

Production of N-β-chloroethyl-N'-p-toluenesulfonylpiperazine:

(III)

(IV)

After refluxing for 72 hours a reaction mixture consisting of 60 g (0.25 mol) of p-toluenesulfonylpiperazine (III), 41 ml (0.5 mol) of 1-bromo-2-chloroethane and 35 ml (0.25 mol) of triethylamine in 1 liter of benzene, the solution was filtered and white needle crystal were obtained from the filtrate. N-β-chloroethyl-N'-p-toluenesulfonylpiperazine 61 g (yield: 79%) was obtained.

EXAMPLE 4

Figure 4:
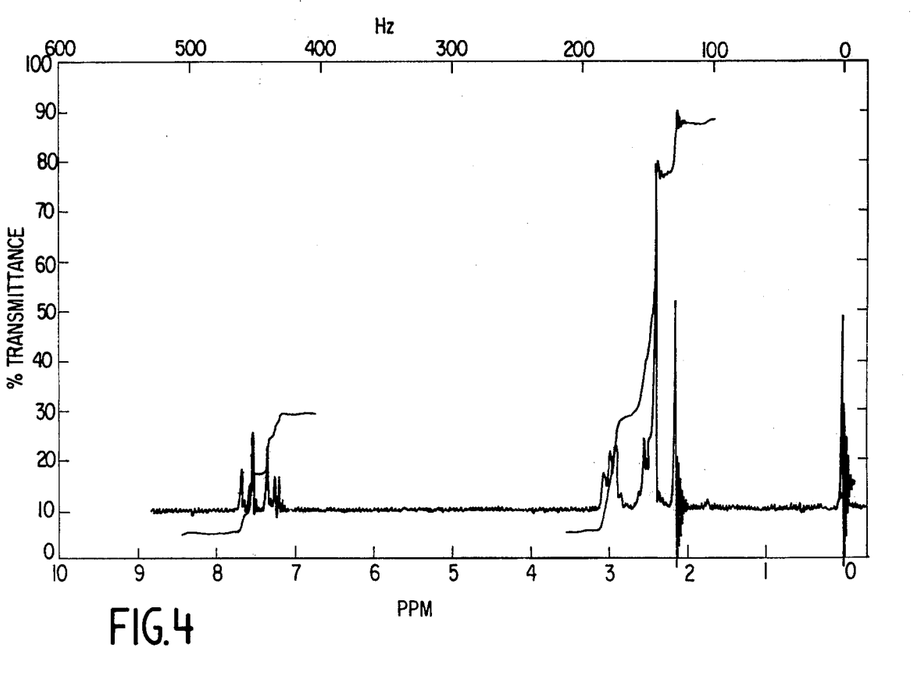

Production of 1,1'-ethylene-bis (4-p-toluenesulfonylpiperazine) corresponding to Compound (VII), $n=1$:

(V)

p-toluenesulfonylpiperazine (III) 48.0 g (0.2 mol), triethylamine 42 ml (0.3 mol), and 1,2-dibromoethane 18.8 g (0.1 mol) were dissolved in 500 ml of 95% ethanol in a one liter three-necked flask equipped with a stirrer and a condenser. The solution was heated to reflux for 12 hours and then cooled to room temperature to precipitate white crystals of 1, 1'-ethylene-bis (4-p-toluenesulfonyl) piperazine (V, $n=1$) 51.2 g (yield: 89% based on (III) ). The compound was recrystallized from N,N-dimethylformamide (DMF) to yield crystals having a M.P. of 255.0°~255.5°C. The structure was confirmed by IR in Nujol (FIG. 3) and the NMR spectrum in $d_6$-DMSO (FIG. 4). Elemental analysis: Calculated: C 56.92%; H 6.72%; N 11.07%. Found: C 56.96%; H 6.90%; N 11.18%.

EXAMPLE 5

Production of 1,1'-ethylene-bis (4-p-toluenesulfonylpiperazine):

A solution of 6.0 g (0.025 mol) p-toluenesulfonyl (III), 7.56 g (0.025 mol) N-β-chloroethyl-N'-p-toluenesulfonylpiperazine, (IV) and 3.5 ml (0.025 mol) triethylamine in 100 ml of 95% ethanol was refluxed for 48 hours. Following the procedures described in Example 4, 8.2 g of white needle crystals of 1,1'-ethylene-bis(4-p-toluenesulfonylpiperzine) (V) (yield 68% based on III) was obtained.

Figure 5:
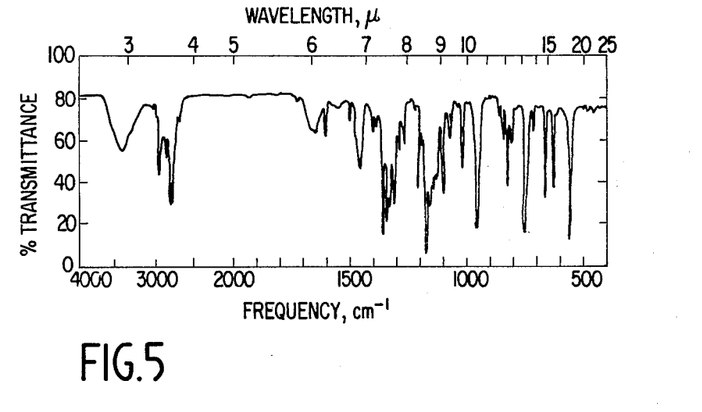
FIGS. 5 and 6 show the IR (KBr tablet) and NMR ($d_6$-DMSO) spectra from Example 6($n$=2)
Figure 6:
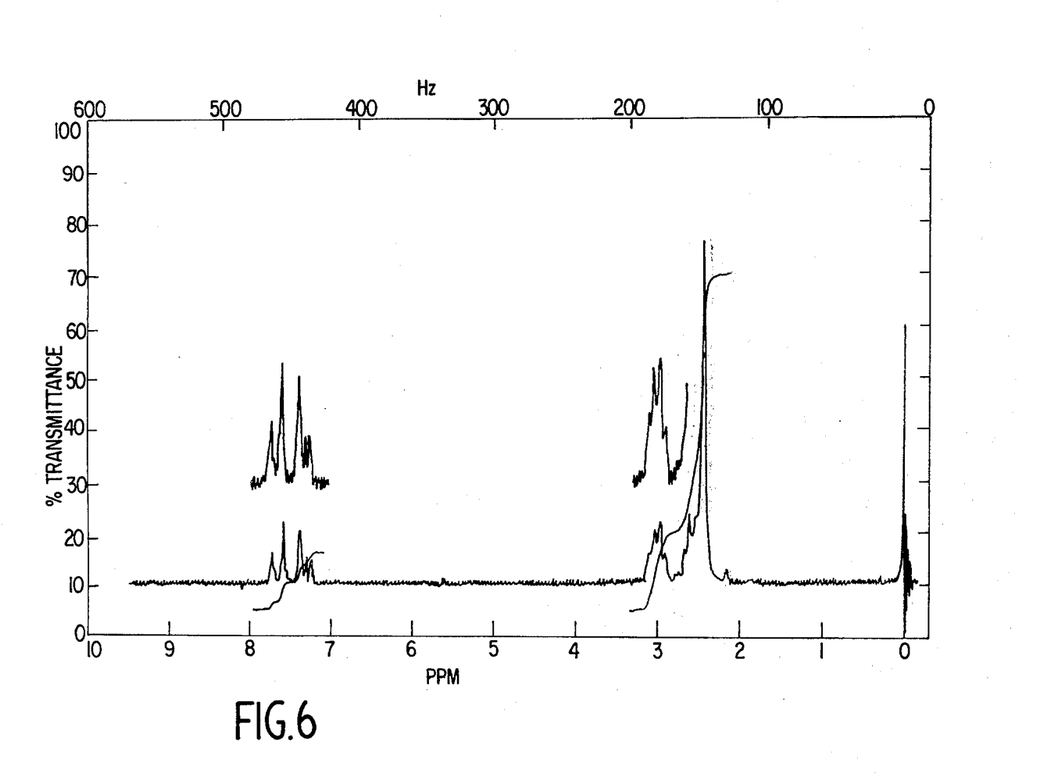

EXAMPLE 6
Production of (VI) (n=2):

37.2 g (0.114 mol) of N-β-chloroethyl-N'-p-toluenesulfonylpiperazine (VI), 5 g (0.058 mol) of piperazine, and 16.0 ml (0.116 mol) of triethylamine in 250 ml 95% ethanol were refluxed for 6 hours. After completion of the reaction and by following the procedure described in Example 4, 26.7 g of a white powder (yield: 86.2% based on piperazine) was obtained. Recrystallization of the white powder from N,N-dimethylformamide (DMF), gave pale yellow needles, M.P. 259.5°~260.5°C. Elemental analysis: Calculated: C 27.26%; H 7.45%; N 13.59%. Found: C 57.57%; H 7.32%; N 13.48%. The IR spectrum (KBr tablet) is shown in FIG. 5 and the NMR spectrum ($d_6$-DMSO) is shown in FIG. 6.

Figure 7:
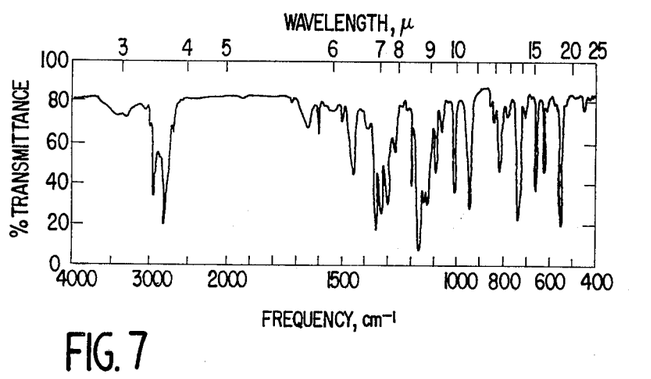
FIGS. 7 and 8 show the IR (KBr tablet) and NMR ($d_6$-DMSO) spectra from Example 7 ($n$=3)
Figure 8:
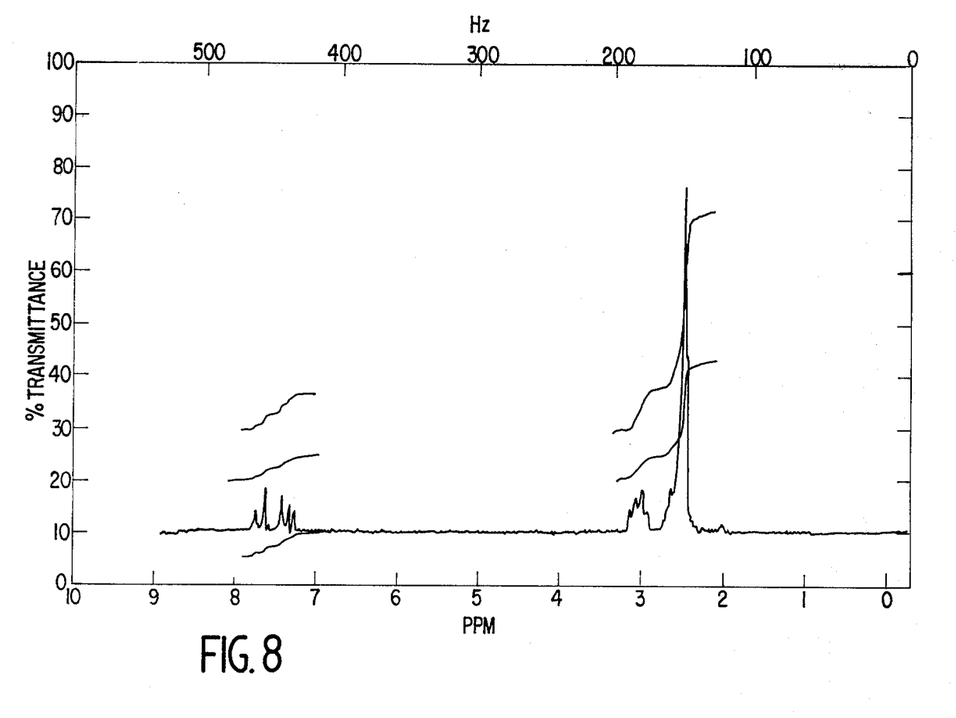
Figure 9:
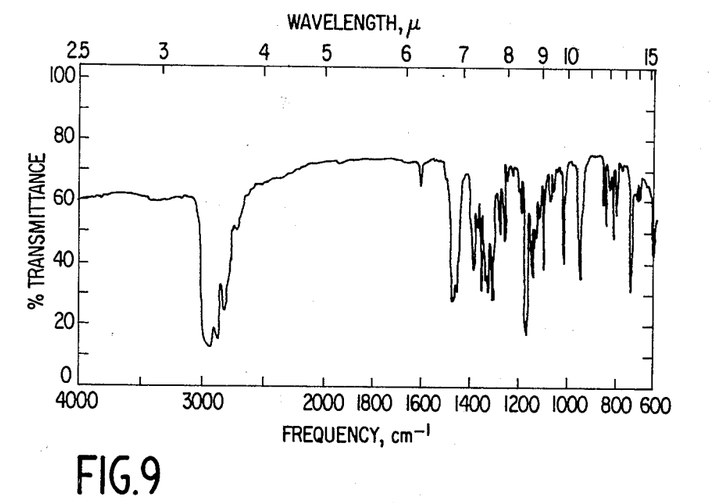
FIGS. 9 and 10 show the IR (Nujol) and NMR ($d_6$-DMSO) spectra from Example 7 ($n$=4)
Figure 10:
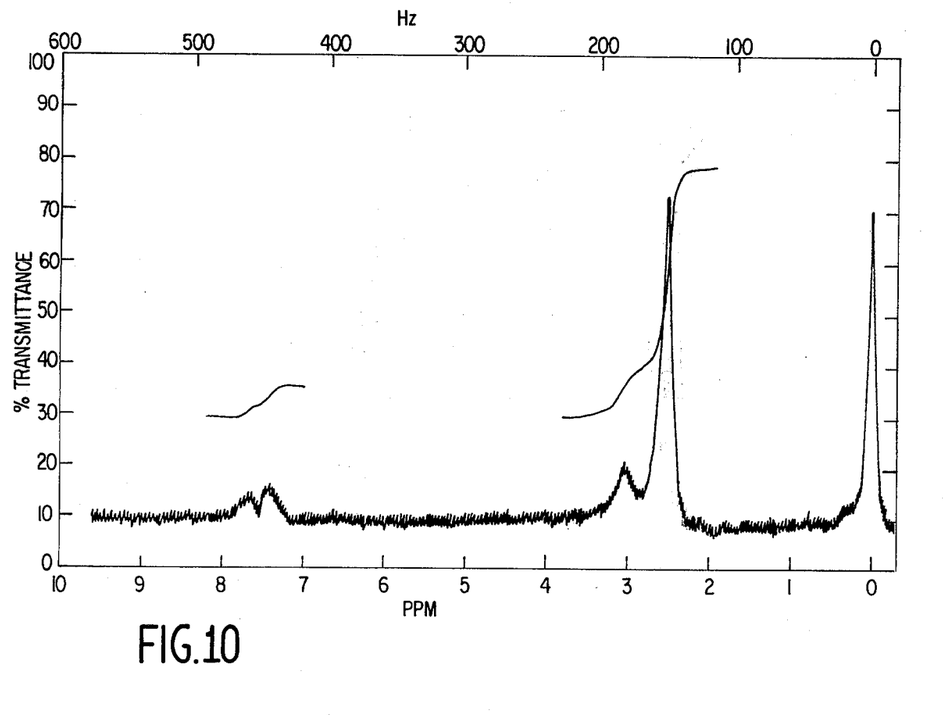

EXAMPLE 7
Production of (VII) (n=3,4,5,6,7):

The procedure of Example 6 was repeated. 95% ethanol was employed as the polar solvent and triethylamine was employed as the acid acceptor. Every oligoamine I with n=1~5 was employed respectively. The mole ratio of each reagent was as follows: Oligoamine (I, n=1) to 5 0.2 mol % in 95% ethanol; triethylamine 1.1 mole to 1 mole of oligoamine I; N-β-chloroethyl-N'-p-toluenesulfonylpiperazine 2.4 moles to 1 mole of oligoamine I. The results were as follows:

a. n=3 melting point: 261°~262°C. Yield: 84.5% (based on oligoamine). The IR spectrum (KBr tablet) is shown in FIG. 7, and the NMR spectrum ($d_6$-DMSO) is shown in FIG. 8. Elemental Analysis: Calculated: C 59.14%; H 8.02%; N 15.32%. Found: C 59.20%; H 8.01%; N 15.39%.

b. n=4 melting point: 262°~264°C. Yield: 90.9%. Elemental analysis: Calculated: C 59.82%; H 3.39%; N 16.60%. Found: C 59.84%; H 8.63%; N 16.90%. The IR spectrum (Nujol) is shown in FIG. 9 and the NMR spectrum ($d_6$-DMSO) is shown in FIG. 10.

c. Following to the procedures described above, the corresponding compounds in which n=5, 6 and 7 respectively were produced and identified by elemental analysis:

n=5  Yield  77.5%  Melting point  250°C decomposition
n=6  Yield  62.6%  Melting point  240°C decomposition
n=7  Yield  60.5%  Melting point  235°C decomposition

17

By repeating the procedures set forth above, compounds with n greater than 7 n can be obtained up to any desired value for n.

EXAMPLE 8

Production of 1,1'-ethylene-bis (N-piperazine) n=1:

(V)

(I, n=1)

Figure 11:
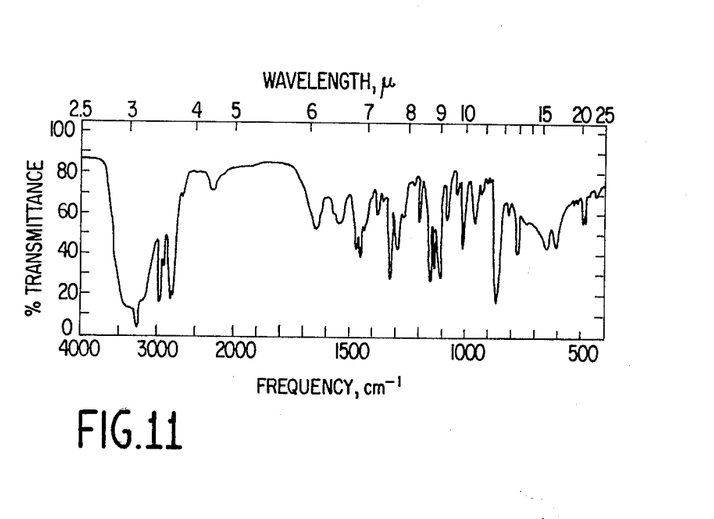
FIGS. 11 and 12 show the IR (KBr tablet) and NMR (CDCl$_3$) spectra from Example 8 ($n$=1)
Figure 12:
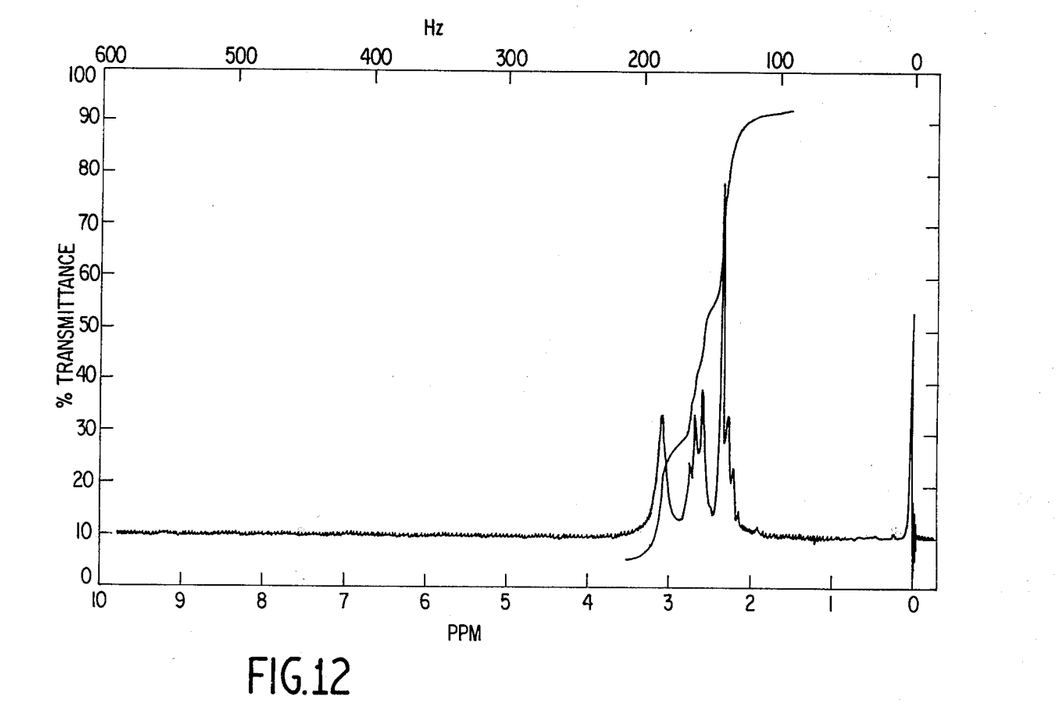

52.28 g (0.1 mol) of 1,1'-ethylene-bis-(4-p-toluenesulfonylpiperazine (V) was suspended in 1.6 liters of isopentanol and heated to reflux. Under reflux 161 g (7 moles) of sodium metal was added portionwise over a period of about 6 hours into the suspension, and heating was continued for a further 6 hours. The reaction mixture was kept standing at room temperature until the mixture solidified. After the addition of 500 ml of water into the mixture, the aqueous layer was removed and concentrated. White needle-crystals were obtained from the concentrate, which were dried under vacuum to give 22.1 g (yield 99.5%) of crude I, n=1, which was recrystallized from diluted ammonia solution (pH 9~11). Melting point 104.0°~105.0°C. The IR spectrum (KBr tablet) is shown in FIG. 11 and the NMR spectrum in CDCl₃ is shown in FIG. 12. Elemental analysis: Calculated: C 60.56%; H 11.20%; N28.24%. Found: C 60.25%; H 11.25%; N 28.10%.

EXAMPLE 9

Figure 13:
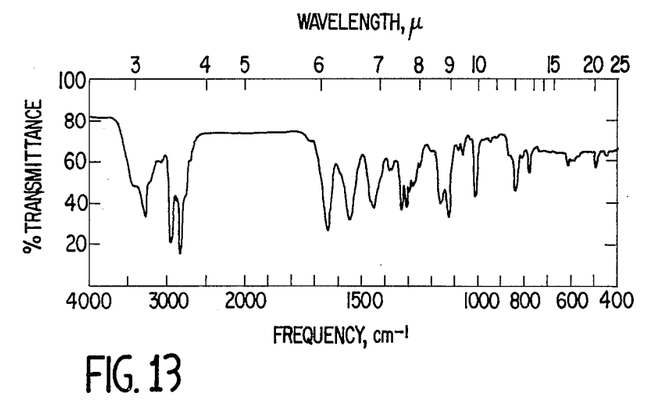
FIGS. 13 and 14 show the IR (KBr tablet) and NMR (CDCl$_3$) spectra from Example 9 ( $n$=2)
Figure 14:
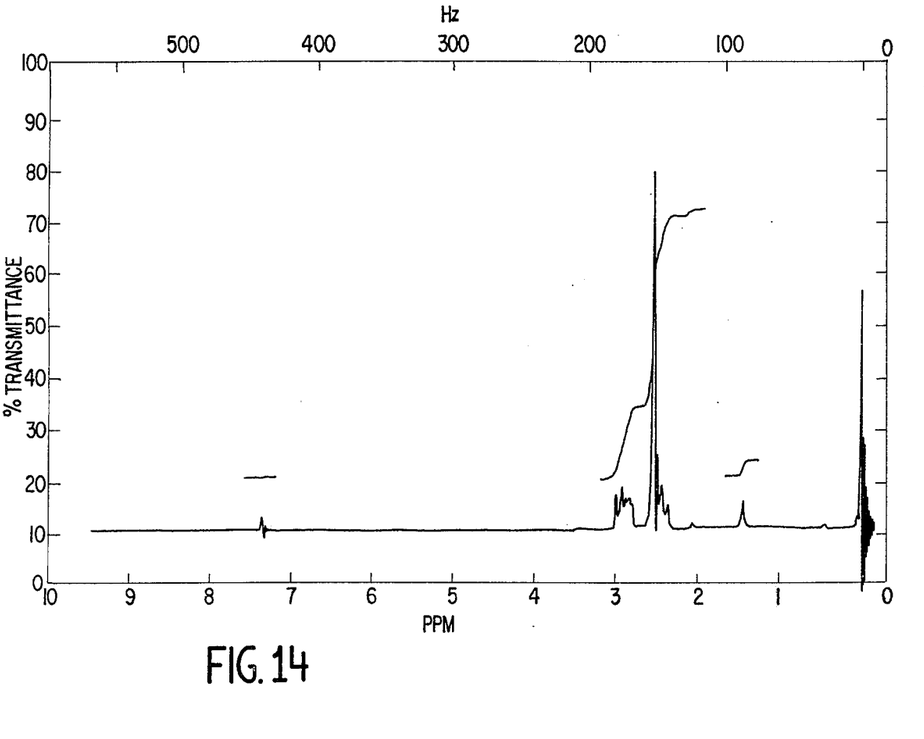
Figure 15:
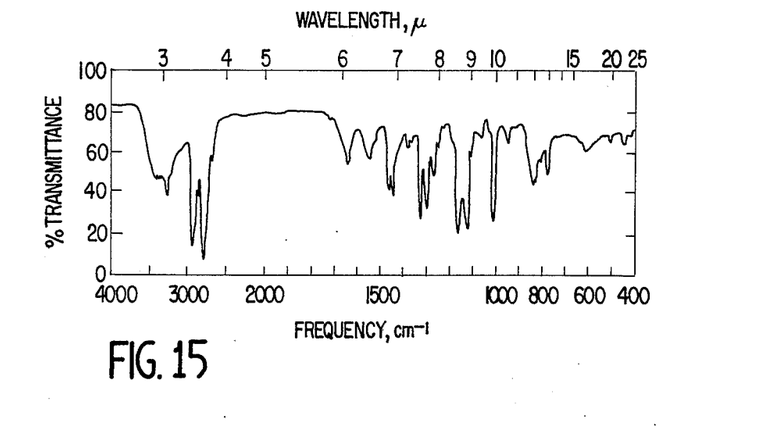
FIGS. 15 and 16 show the IR (KBr tablet) and NMR (CDCl$_3$) spectra from Example 9 ($n$=3).
Figure 16:
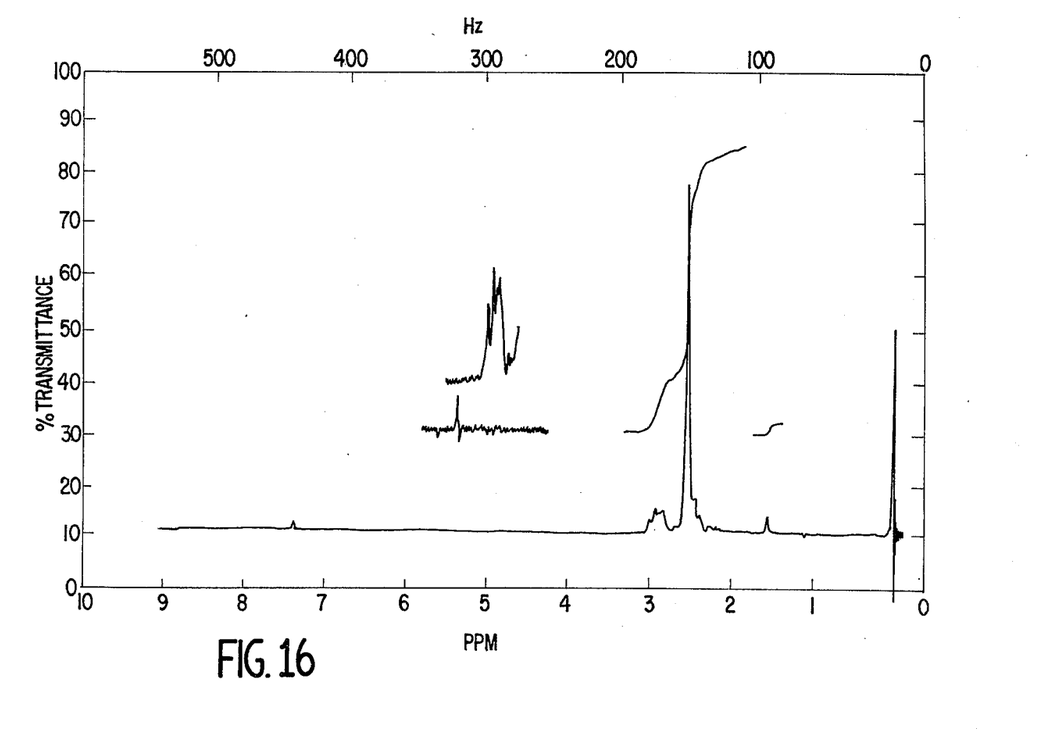

Production of (I) n=2,3,4,5,6,7:

Following the procedure described in Example 8, each oligomer (I) ( n=2,3,4,5,6,7) was obtained with yields of greater than 95% by employing sodium as a reducing agent added little by little into the alcohol solution to a total amount of 70~100 fold molar excess with respect to VII. Purification by recrystallizing the compounds from diluted ammonia solution gave crystalline compounds. Following the same procedures, every corresponding compound VII wherein n=2,3,4,5,6, and 7 was obtained.

a. n=2 Melting point: 133.0°~133.5°C. The IR spectrum (KBr tablet) is shown in FIG. 13 and the NMR spectrum (CDCl₃) is shown in FIG. 14. Elemental analysis: Calculated: C 62.51%; H 11.06%; N 27.05%. Found: C 62.50%; H 11.42%; N 26.95%.

b. n=3 Melting point: 155.0°~156.0°C. The IR spectrum (KBr tablet) is shown in FIG. 15 and the NMR spectrum (CDCl₃) is shown in FIG. 16. Elemental analysis: Calculated: C 62.51%; H 10.99 %; N 26.50%. Found: C 62.60%; H 11.21%; N 26.57%.

c. Following the procedures set forth above, the following compounds were produced and identified by elemental analysis.

| | | |
|---|---|---|
| n=4 | Melting point: | 164.5 ~ 165.5°C |
| n=5 | Melting point: | 180 ~ 182°C |
| n=6 | Melting point: | 185°C colorized and decomposed |
| n=7 | Melting point: | 182°C colorized and decomposed |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What I claim is:

1. A compound selected from the group consisting of oligoethylenepiperazines of the formula wherein $n$ is a positive integer of 2 through 7 inclusive, the acid addition salts thereof and the quaternary salts thereof wherein at least one tertiary amino group is in quaternary form.

2. A compound according to claim 1 in the form of an acid addition salt.

3. A compound according to claim 1 wherein at least one tertiary amino group thereof is in the form of a quaternary salt.

4. A compound according to claim 1 wherein $n = 2$.

5. A compound according to claim 1 wherein $n = 3$.

6. A compound according to claim 1 wherein $n = 4$.

7. A compound according to claim 1 wherein $n = 5$.

8. A compound according to claim 1 wherein $n = 6$.

9. A compound according to claim 1 wherein $n = 7$.

* * * * *